United States Patent [19]

Vangedal

[11] 4,246,262
[45] Jan. 20, 1981

[54] DERIVATIVES OF AMIDINOPENICILLANIC ACID

[75] Inventor: Ib S. Vangedal, Lyngby, Denmark

[73] Assignee: Leo Pharmaceutical Products, Ltd. A/S, Ballerup, Denmark

[21] Appl. No.: 913,671

[22] Filed: Jun. 8, 1978

[30] Foreign Application Priority Data

Jun. 21, 1977 [GB] United Kingdom ............... 25992/77

[51] Int. Cl.³ .................. A61K 31/33; A61K 31/425; C07D 499/02; C07D 501/14
[52] U.S. Cl. .............................. 424/244; 260/245.2 R; 260/239.1; 424/246; 424/267; 424/270; 424/271; 542/416; 542/419; 542/422
[58] Field of Search ....................... 542/422, 416, 419; 424/200, 246, 270, 271, 244, 267; 260/239.1, 306.7 C, 245.2

[56] References Cited

U.S. PATENT DOCUMENTS

| | | | |
|---|---|---|---|
| 3,755,588 | 8/1973 | Lund | 424/271 |
| 3,957,764 | 5/1976 | Lund | 260/240 G |

FOREIGN PATENT DOCUMENTS

| | | | |
|---|---|---|---|
| 1303491 | 1/1973 | United Kingdom | 260/240 G |
| 1315566 | 5/1973 | United Kingdom | 260/240 G |
| 1405886 | 9/1975 | United Kingdom | 260/240 G |
| 1427139 | 3/1976 | United Kingdom | 260/240 G |

*Primary Examiner*—Howard T. Mars
*Assistant Examiner*—Vera C. Clarke
*Attorney, Agent, or Firm*—Dann, Dorfman, Herrell and Skillman

[57] ABSTRACT

The present invention relates to new 6β-amidinopenicillanic acids of the formula:

$$\begin{array}{c} R_1 \\ \diagdown \\ N-A-X-B-W-CH=N-\underset{\underset{O=C-N}{|}}{\overset{H}{\underset{|}{C}}}-\overset{H}{\underset{|}{C}}\diagdown\underset{CH}{\overset{S}{\diagup}}\diagdown\underset{CH_3}{\overset{CH_3}{C}} \\ R_2 \\ \qquad\qquad\qquad\qquad COOH \end{array} \quad I$$

in which X is oxygen or sulphur, —A— is aliphatic hydrocarbon, or a single bond, —B— is aliphatic hydrocarbon, or a single bond; $R_1$ and $R_2$ stand for hydrogen, lower alkyl, phenyl or phenyl-lower alkyl; or $R_2$ is acyl or guanyl; or $R_1$ and $R_2$ together with the nitrogen atom can form a monocyclic, saturated ring or represent $$\begin{array}{c} R_3 \\ \diagdown \\ N-CH=, \\ \diagup \\ R_4 \end{array}$$

in which $R_3$ and $R_4$ each stands for hydrogen, lower alkyl, phenyl, or phenyl-lower alkyl, or $R_3$ and $R_4$ together with nitrogen form a monocyclic, saturated ring; —W— stands for $$-N-;\quad -\langle\phantom{N}\rangle N-\quad \text{or}\quad -\langle\phantom{N}\rangle\langle\phantom{N}\rangle N-;$$

which represent saturated, monocyclic, bicyclic or spirocyclic ring systems, respectively; salts of the compounds of formula I, and easily hydrolyzable, esters thereof, and salts of such esters; the invention further relating to methods of producing the compounds; to intermediates in their preparation; to pharmaceutical compositions containing the compounds; and to dosage units thereof, and to their use.

The compounds of the present invention are active against a variety of pathogenic microorganisms, including gram-positive and gram-negative bacteria.

46 Claims, No Drawings

DERIVATIVES OF AMIDINOPENICILLANIC ACID

The present invention relates to new 6β-amidinopenicillanic acids; pharmaceutically acceptable, nontoxic salts, easily hydrolyzable esters thereof and pharmaceutically acceptable non-toxic salts of such esters; to methods of producing the compounds; to intermediates in their preparation; to pharmaceutical compositions containing the compounds; and to dosage units thereof, and to their use.

The compounds of the invention are carboxylic acids represented by the general formula

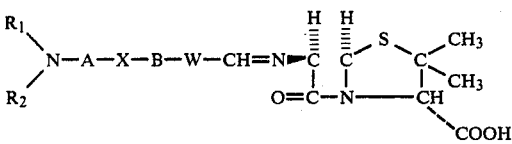

in which X stands for an oxygen or a sulphur atom, —A— stands for a straight or branched, aliphatic hydrocarbon chain, containing from 2 to 4 carbon atoms, or —A— can be a single bond, and —B— stands for a straight or branched, saturated or unsaturated aliphatic hydrocarbon radical, containing from 1 to 4 carbon atoms, or —B— can be a single bond; $R_1$ and $R_2$ stand for hydrogen, or a lower alkyl radical with from 1 to 4 carbon atoms, a phenyl or phenyl-lower alkyl radical; $R_2$ further stands for an acyl radical derived from a mono- or dibasic carboxylic acid, sulphuric acid, a sulphonic acid, a sulphinic acid, phosphoric acid, or a phosphonic acid, or $R_2$ can represent an unsubstituted or substituted carbamoyl, guanyl and guanylcarbamoyl radical; $R_1$ and $R_2$ together with the nitrogen atom can form a monocyclic, saturated ring having from 4 to 8 carbon atoms; furthermore $R_1$ and $R_2$ together can represent a radical of the formula

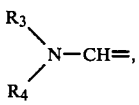

in which $R_3$ and $R_4$ each stands for hydrogen, lower alkyl, phenyl, or phenyl-lower alkyl radicals, or in which $R_3$ and $R_4$ together with the nitrogen atom form a monocyclic, saturated ring having from 4 to 8 carbon atoms; and in which the radical —W— stands for the groupings

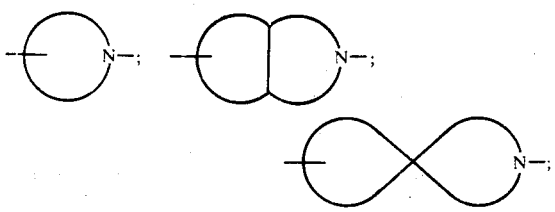

which represent saturated, monocyclic, bicyclic or spirocyclic ring systems, respectively, containing from 4 to 11 carbon atoms in total; and salts of the compounds of the formula I with pharmaceutically acceptable, non-toxic organic and inorganic acids or bases, and easily hydrolyzable, pharmaceutically acceptable, non-toxic esters of the penicillanic acid derivatives of formula I, including diesters of the formula II:

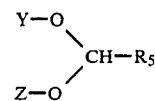

in which Y and Z can be the same or different and stand for an acyl radical of one of the compounds of formula I, and Z furthermore can be the acyl radical of other known β-lactam derivatives, $R_5$ stands for hydrogen, methyl, ethyl, or phenyl, and salts of such esters with pharmaceutically acceptable, non-toxic acids or bases.

More particularly, $R_1$ and $R_2$ can be hydrogen or a lower alkyl radical having from 1 to 4 carbon atoms as, for instance, methyl, ethyl, propyl, isopropyl, n-butyl, sec-butyl, isobutyl or tert-butyl, or phenyl, phenylmethyl or phenylethyl.

Similarly, $R_2$ when standing for an acyl radical, can e.g. be formyl, acetyl, propionyl, butyryl, isobutyryl, valeryl, isovaleryl, trimethylacetyl, capropyl, glycolyl, benzoyl, phenylacetyl, phenoxyacetyl, glycyl, phenylglycyl or acyl radicals of other amino acids, heterocyclically substituted acyl, e.g. nicotinoyl, or

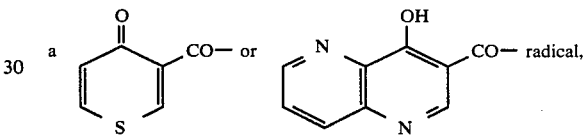

or a monoacyl radical derived from a dibasic acid such as oxalic, malonic, succinic, maleic, fumaric, tartaric, malic or phthalic acids; and when $R_2$ stands for a substituted carbamoyl, guanyl, or guanylcarbamoyl radical, the substituents can be e.g. lower alkyl or phenyl radicals. Further $R_2$ stands for an acyl radical derived from sulphuric acid, a sulphonic, sulphinic, phosphoric or a phosphonic acid such as toluenesulphonic acid, methane- or ethanesulphonic acid, toluenesulphinic acid, lower alkylphosphonic acids etc.

In the formula above $R_3$ and $R_4$ can more specifically be lower alkyl with from 1 to 4 carbon atoms or phenyl-lower alkyl in which the alkyl radical has from 1 to 4 carbon atoms. $R_1$ and $R_2$, or $R_3$ and $R_4$ when taken together with the adjacent nitrogen atom, more particularly form a pyrrolidyl, piperidyl, hexahydro-1H-azepin-1-yl or hexahydro-1(2H)-azocin-1-yl or a octahydro-1H-azonin-1-yl radical.

More particularly, —A— can be a single bond or an ethylene, propylene, butylene, isopropylene, isobutylene, sec-butylene radical, and —B— besides being a single bond can be a methylene, ethylene, propylene, trimethylene, tetramethylene, propylidene, methyltrimethylene, propenylene, butenylene, methylpropenylene, propynylene, butynylene, or methylpropynylene radical.

More particularly the grouping —W—, representing saturated monocyclic, bicyclic or spirocyclic ring systems can be pyrrolidyl, piperidyl, hexahydro-1H-azepinyl, hexahydro-1(2H)-azocinyl, octahydro-1H-azonin-1-yl, azacyclododecanyl, 3-azabicyclo[3.1.0]hexanyl, 5-azaspiro[2.4]heptanyl, 3-azabicyclo[4.1.0]heptanyl, 3-azabicyclo[3.2.0]heptanyl, 6-azabicyclo[3.1.1]heptanyl, 7-azabicyclo[4.2.0]octanyl, 2-azabicyclo[2.2.2]octanyl, 1-azaspiro[5.5]undecanyl, 2-, and 3-azabicyclo[3.3.1]nonanyl 2-azaspiro[4.6]undecanyl, 2-azabicyclo[3.2.1]octanyl, 3-azabicyclo[3.2.1]octanyl, 6-azabicyclo[3.2.1]octanyl, 1-azaspiro[4.5]decanyl, 2-azaspiro[4.5]decanyl, 2-azabicyclo[3.2.2]nonanyl, 3-azabicyclo[4.1.1]octanyl, 2-azabicyclo[2.2.1]heptanyl, 2-azabicyclo[4.3.1]decanyl, 8-azaspiro[4.5]decanyl, 2-azaspiro[5.5]undecanyl, 3-azaspiro[5.5]undecanyl, 3-azabicyclo[3.1.1]heptanyl, 2-azabicyclo[4.2.0]octanyl, 2-azaspiro[4.4]nonanyl, 8-azabicyclo[4.3.1]decanyl, 4-azabicyclo[5.3.0]decanyl, 3-azabicyclo[3.3.0]octanyl, 8-azabicyclo[4.3.0]nonyl, the examples above, however, not being construed as limiting the invention.

The salts of the compounds of the invention are in addition to their inner salts (zwitterions) mono-or dibasic salts, formed with non-toxic, pharmaceutically acceptable acids such as hydrochloric acid, phosphoric acid, nitric acid, p-toluenesulphonic acid, acetic acid, propionic acid, citric acid, tartaric acid, maleic acid etc., but any pharmaceutically acceptable, non-toxic, inorganic or organic acid can be used as well.

Also included in the invention are salts with pharmaceutically acceptable, non-toxic, inorganic or organic bases, e.g. alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)-amine or tris-(2-hydroxyethyl)-amine, cycloalkylamines, for example dicyclohexylamine, or benzylamines, for example N,N'-dibenzyl-ethylenediamine, and dibenzylamine, without these examples limiting the invention. Thus for instance other antibiotics with acid or basic character can be used as components of such salts of the compounds of formula I.

The easily hydrolyzable, pharmaceutically acceptable esters of the new compounds are the well known types of esters, e.g. acyloxyalkyl esters, such as alkanoyloxyalkyl esters, e.g. acetoxymethyl and pivaloyloxymethyl esters and the corresponding 1-acetoxyethyl and 1-pivaloyloxyethyl esters, alkoxycarbonyloxyalkyl esters, e.g. methoxycarbonyloxymethyl and -ethoxycarbonyloxyethyl esters, lactonyl esters, e.g. phthalidyl esters, or lower alkoxymethyl esters. Other interesting acyloxyalkyl esters are within the scope of the invention, e.g. such esters in which the acyl group is a radical derived from a β-lactam derivative, such as a penicillin, a cephalosporin, an amidinopenicillanic acid, an amidino-Δ³-cephem-carboxylic acid or clavulanic acid, which esters when hydrolyzed in the host may give rise to enhanced effect. Also other esters can be useful, e.g. the benzyl ester, the cyanomethyl ester, and 1-carbalkoxy-2-oxopropyl esters.

Appropriately the esters above can be prepared and used in the form of their salts with pharmaceutically acceptable, non-toxic, inorganic or organic acids or bases.

When the side chain or the ester group contain one or more asymmetric carbon atoms or double bonds giving rise to cis-trans isomerism the compounds of formula I and their esters exist in several diastereomeric forms. The invention comprises all of these forms as well as mixtures thereof. The penicillanic acid moiety has the steric configuration indicated in the formula I.

A series of substituted 6β-amidinopenicillanic acids, their salts and easily hydrolyzable esters are disclosed in the British Pat. No. 1,293,590 and other easily hydrolyzable esters of the compounds of British Pat. No. 1,293,590 have been disclosed in the British Pat. No. 1,335,718, and other patents.

The compounds of the present invention are active against a variety of pathogenic microorganisms, including gram-positive and gram-negative bacteria. Of special interest is the activity against certain gram-negative bacteria. Within the scope of this invention are compounds in which —A— stands for a single bond or for a carbon chain with from 2 to 4 carbon atoms, and in which the radical —W— have from 4 to 8 carbon atoms in the

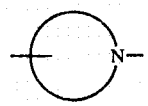

grouping and a maximum of 7 carbon atoms in the individual rings of the bicyclic and spirocyclic groupings

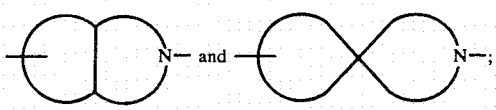

Generally, such compounds are preferred in which —B— is not attached to a carbon atom adjacent to the nitrogen atom of the monocyclic ring system.

The table below indicates compounds of the invention corresponding to formula I (—W— being a monocyclic ring) in which $R_1$, $R_2$, —A—, X, B and the numbers of the carbon atoms in the ring (n) are as follows:

| $R_1$ | $R_2$ | -A- | n | X | B |
|---|---|---|---|---|---|
| H | H | propylene | 4 | O | ethylene |
| H | acetyl | trimethylene | 4 | O | methylene |
| ethyl | H | tetramethylene | 4 | S | methylene |
| methyl | propionyl | 1,1-dimethylethylene | 4 | O | single bond |
| H | H | ethylene | 4 | S | ethylidene |
| butyl | butyl | propylene | 4 | S | methylene |
| methyl | H | trimethylene | 5 | S | ethylene |
| H | guanyl | tetramethylene | 5 | S | methylene |
| H | H | ethylene | 5 | O | methylene |
| isopropyl | H | tetramethylene | 5 | O | single bond |
| H | H | ethylene | 5 | S | ethylidene |
| H | acetyl | tetramethylene | 5 | S | methylene |
| methyl | methyl | tetramethylene | 5 | S | methylene |
| H | methyl | trimethylene | 6 | O | propylene |
| butyl | H | ethylene | 6 | S | methylene |
| H | H | propylene | 6 | O | ethylidene |
| methyl | tosyl | ethylene | 6 | O | single bond |
| H | acetyl | ethylene | 6 | S | methylene |
| ethyl | ethyl | propylene | 5 | S | methylene |
| H | H | single bond | 5 | O | ethylene |
| ethyl | ethyl | ethylene | 5 | S | ethylene |
| H | H | trimethylene | 6 | O | single bond |
| H | guanyl | ethylene | 6 | S | methylene |
| methyl | guanyl | propylene | 6 | O | methylene |
| H | H | trimethylene | 7 | S | ethylidene |
| H | acetyl | 2-methyltri- | 7 | S | methylene |

-continued

| R₁ | R₂ | -A- | n | X | B |
|---|---|---|---|---|---|
| methyl | methyl | methylene tetramethylene | 7 | S | methylene |
| methyl | H | ethylene | 7 | O | trimethylene |
| H | H | ethylene | 7 | O | ethylene |
| H | carbamoyl | ethylene | 7 | O | single bond |
| butyl | H | propylene | 7 | O | single bond |
| H | H | propylene | 7 | S | methylene |
| H | H | ethylene | 8 | O | ethylene |
| H | acetyl | ethylidene | 8 | O | methylene |
| H | guanyl | ethylene | 8 | O | single bond |
| methyl | H | ethylene | 8 | S | methylene |
| H | guanyl-carbamoyl | ethylene | 8 | S | methylene |
| H | H | propylene | 8 | O | methylene |
| H | hemi-succinyl | ethylidene | 8 | S | single bond |
| H | methane-sulphonyl | ethylene | 8 | S | single bond |

The table below indicates compounds of the invention corresponding to formula I (—W— being a bicyclic ring) in which $R_1$, $R_2$, —A—, X, B, and the number of carbon atoms in the rings are as follows, where $n_1$ refers to the heterocyclic part of the ring system, and $n_2$ refers to the total number of carbon atoms in the ring system

| R₁ | R₂ | -A- | n₁ | n₂ | X | B |
|---|---|---|---|---|---|---|
| methyl | H | ethylene | 3 | 7 | O | single bond |
| H | H | trimethylene | 6 | 7 | S | methylene |
| H | H | propylene | 6 | 7 | S | ethylidene |
| H | propionyl | tetramethylene | 4 | 6 | S | methylene |
| ethyl | H | trimethylene | 4 | 7 | O | single bond |
| methyl | methyl | propylene | 5 | 7 | S | ethylene |
| N,N-dimethylamino-methylene | | ethylene | 6 | 9 | O | methylene |
| H | H | ethylene | 4 | 7 | O | single bond |
| ethyl | ethyl | ethylene | 5 | 8 | O | single bond |
| H | carbamoyl | trimethylene | 4 | 6 | S | methylene |

The table below indicates compounds of the invention corresponding to formula I (—W— being a spirocyclic ring) in which $R_1$, $R_2$, —A—, X, B, and the number of carbon atoms in the rings are as follows, where $n_1$ refers to the heterocyclic part of the ring system, and $n_2$ refers to the total number of carbon atoms in the ring system.

| R₁ | R₂ | -A- | n₁ | n₂ | X | B |
|---|---|---|---|---|---|---|
| H | H | propylene | 4 | 9 | S | methylene |
| methyl | methyl | ethylene | 4 | 9 | S | ethylidene |
| dimethyl-aminomethylene | | methylene | 4 | 10 | O | methylene |
| methyl | H | ethylene | 5 | 10 | S | ethylene |
| ethyl | ethyl | trimethylene | 5 | 10 | O | single bond |
| H | H | propenylene | 5 | 9 | O | ethylidene |

The above examples, however, shall in no way be construed as limiting the invention.

In the table below, the antibacterial activity of the compound of Example 2 is compared to that of the known compounds Ampicillin and Mecillinam.

In the table IC₅₀ means the concentration required for 50 percent inhibition.

TABLE

| Organism | IC₅₀ (μg/ml) Ampicillin | Mecillinam | Compound of Example 2 |
|---|---|---|---|
| Pseudomonas aeruginosa BA 2 Leo strain | >100 | >100 | 50 |
| Pseudomonas aeruginosa PS 18s | 50 | >100 | 40 |
| E.coli HA 2 Leo strain | 1.3 | 0.016 | 0.05 |
| E.coli W3110 (R$_{TEM}$) | >100 | 2.0 | 1.6 |
| Klebsiella pneumoniae ATCC 10273 | 79 | ~1 | 0.32 |
| Enterobacter cloacae P 99 | >100 | 0.1 | 0.063 |
| Salmonella typhimurium NCTC 5710 | o.4 | 0.05 | 0.05 |
| Salmonella cholerasuis NCTC 5735 | 0.25 | 0.05 | 0.05 |

The invention also comprises methods for the preparation of the compounds of the invention. In one embodiment the compounds are prepared by reacting a reactive derivative of an amide or a thioamide of the general formula III:

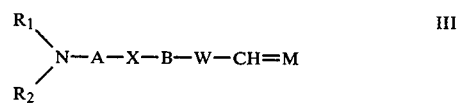

in which $R_1$, $R_2$, —A—, —B—, X, and —W— are as defined hereinbefore, or

is, if necessary, protected or replaced by a nitro or an azido group, or a halogen atom, whereas M stands for oxygen or sulphur, with a 6-aminopenicillanic acid derivative of the general formula IV

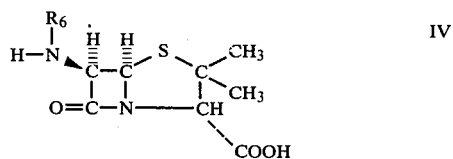

in which $R_6$ is hydrogen or a trialkylsilyl group; or a salt thereof, or with an ester of the intermediate of formula IV, e.g. a trialkylsilyl, benzyl, cyanomethyl or a 1-carbalkoxy-2-oxopropyl ester or an easily hydrolyzable ester as defined above or an ester of the formula V:

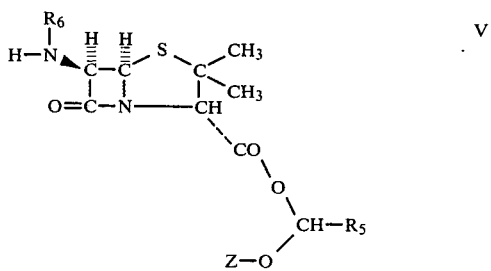

in which $R_5$, $R_6$, and Z have the meanings hereinbefore defined.

If a silyl ester of the intermediate of formula IV is used, the reaction must be followed by a hydrolysis or alcoholysis to provide the free acids of the invention, which also may be obtained by cleavage of the other esters obtained by the reaction.

In the case of 1-carbalkoxy-2-oxopropyl esters, conversion to the corresponding free acid can be accomplished by treatment with nitrosating reagents such as sodium nitrite or alkyl nitrite.

The preparation of the above mentioned 6-aminopenicillanic acid derivatives is known from the literature.

In the case where in the compounds of formula I one or both of $R_1$ and $R_2$ stand for hydrogen or

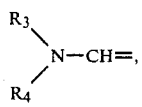

$R_3$ and/or $R_4$ being hydrogen, it can be necessary to protect the

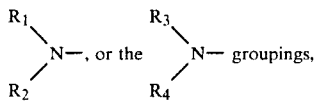

temporarily during the process with protecting groups as more particularly described below. Alternatively, instead of the starting materials of formula III can be used a compound which instead of the

grouping has a group, e.g. a nitro or an azido group, or a halogen atom, which after the reaction with the compound of formulae IV or V can be transformed into an amino group under mild conditions. These intermediates are also new compounds constituting as such a part of this invention. Also they have in themselves interesting antibacterial properties, especially the azido compounds.

The starting materials of formula III can be prepared by conventional methods known to the man skilled in the art. The reactive derivatives of these starting materials are in the following described more in detail.

The amides or thioamides of formula III, can be transformed by well-known methods into reactive derivatives such as acid amide halides or acid amide acetals or iminium-ethers or -thioethers, e.g. acid amide dialkyl sulphate complexes or complexes with the well-known Meerwein reagent (triethyloxonium tetrafluoroborate). The acid amide halides are preferably the chlorides or bromides and they can be prepared by treating the amides with halogenating agents. It is preferred to use halogenating agents which throughout the reaction form gaseous by-products, such as phosgene, oxalyl halides, or thionyl halides, but others may also be used. The reaction can be performed in an inert, dry, organic solvent, e.g. ether or toluene, in which the amide halide will in most cases be insoluble and from which it can be isolated by filtration after the reaction is completed. The acid amide halides are hygroscopic and rather unstable and are therefore preferably used in the next step without purification. However, the amide halide may also be prepared in e.g. alcohol-free chloroform solution and used directly for the next step, advantage being taken of the harmless character of the gaseous by-products ($CO$, $CO_2$, $SO_2$, $COS$).

Useful acid amide dialkyl sulphate complexes as intermediates can be prepared by treating the corresponding amides with a dialkyl sulphate, preferably dimethyl sulphate, under well-known conditions. By treating the acid amide dialkyl sulphate complexes or acid amide halides with a sodium $C_1$ to $C_6$ alcoholate, e.g. sodium methoxide, acid amide acetals of the general formula VI:

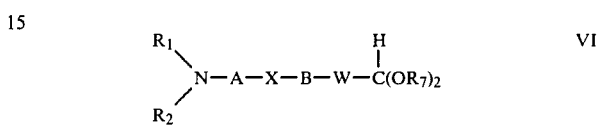

in which $R_1$, $R_2$, A, B, X and —W— have the meanings hereinbefore defined, or

is, if necessary, protected or replaced by a nitro or an azido group or a halogen atom, whereas $R_7$ stands for an alkyl group containing from 1 to 6 carbon atoms, are formed, which acetals may also be used in the preparation of compounds of formula I.

When acid thioamides are used as starting materials, a reactive derivative in form of an acid thioamide alkyl halide complex can be formed by treatment with an alkyl halide, e.g. a $C_1$ to $C_6$ alkyl iodide. This reaction is well known from the chemical literature.

The reaction conditions for the reaction between the amide derivative and the compound of formulae IV or V depend on the reaction components used in the process. For instance, when an acid amide acetal or a dialkyl sulphate complex or another iminium ether or thioether is used in the reaction with the compound of formulae IV or V, the reaction is performed in an organic solvent and at a temperature depending upon the reaction components. When an acid amide halide is used, the reaction is usually performed in an inert organic solvent, which is dry and free from traces of alcohol, preferably chloroform, in which the reaction components are soluble, but solvents in which the starting materials are insoluble, e.g. ether, may also be used. The reaction is performed with cooling and, in the presence of at least one equivalent of a tertiary amine, for example trimethylamine, triethylamine, N,N-diisopropylethylamine or N-methylmorpholine.

The reaction time depends on the reactants, the temperature and the solvents used in the process.

In the preparation of compounds of formula I, it is also possible to use as starting material a trialkylammonium salt of 6-APA, which is reacted with e.g. an acid amide acetal under the same conditions as mentioned above. Such reactions are known from the specification to our British Pat. No. 1 417 099.

In another embodiment the compounds of the present invention can be prepared by reacting an amine of the formula VII:

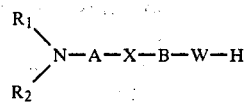

in which R$_1$, R$_2$, A, X, B, and —W— are as hereinbefore defined, or

is, if necessary, protected or replaced by nitro or azido, or a halogen atom, with a 6-N-alkoxymethyleneaminopenicillanic acid ester obtained either by reacting an ester of a compound of formulae IV, or a compound of formula V, with a 1,1-dihalomethyl-alkyl ether, preferably 1,1-dichlorodimethyl ether, in the presence of a tertiary organic base. The reaction can be performed without isolation of the intermediate formed by the process, which in the example mentioned above is supposed to be a 6-N-methoxymethylene derivative of the starting material. The reactions are performed below or at room temperature and in the presence of an inert solvent, e.g. chloroform, or ether. However, a more favourable method to obtain a 6-alkoxymethyleneaminopenicillanic acid ester consists in reacting a solution of an ester of a compound of formula IV or a compound of formula V with a formimidic ester hydrochloride, preferably isopropyl formimidate hydrochloride, preferably at room temperature and for the time necessary to accomplish the reaction. Ammonium chloride is thereby precipitated leaving a solution of a 6-alkoxymethyleneaminopenicillanic acid ester.

The reaction products of formula I can be purified and isolated in usual manner and may be obtained either in the free state or in the form of salts or esters. The free acids can also be obtained from the esters by chemical or enzymatic hydrolysis or a mild hydrogenolysis, and if the free acids are the reaction products, the salts and esters can be prepared therefrom by methods known from the literature.

Protection of the amino groups

or, if present, the

of the formulae I, VI, and VII may, if necessary, take place by methods known from the peptide chemistry. Amongst many known and suitable protecting groups can be mentioned a benzyloxycarbonyl radical, a p-halo-, p-nitro-, or p-methoxybenzyloxycarbonyl radical, a β,β,β-trichloroethyloxycarbonyl or an allyloxycarbonyl radical; or a sulphur containing radical, such as a triphenylmethylsulphenyl radical, an arylsulphenyl radical, e.g. an o-nitrophenylsulphenyl radical; a triphenylmethyl radical, a tertiary butoxycarbonyl radical, or a radical obtained by reacting the free amino group with a β-dicarbonyl compound such as acetylacetone, benzoylacetone or acetoacetic esters or amides to form enamines, or to form Schiff bases with e.g. formaldehyde, acetaldehyde etc. Furthermore the R$_1$R$_2$N— or R$_3$R$_4$N— groupings may be protected in form of a salt, e.g. a hydrochloride. In general any group which can be split off by reduction, by mild acid hydrolysis or by other mild reactions not damaging the β-lactam ring will be suitable.

Whatever protection of the amino group has been used or, alternatively, whatever conventional replacement of the amino group has been used, the amino group can be established by well-known methods, such as hydrogenation, hydrolysis or aminolysis.

In another embodiment of the invention compounds of formula I can be obtained by reacting a compound of formula VIII

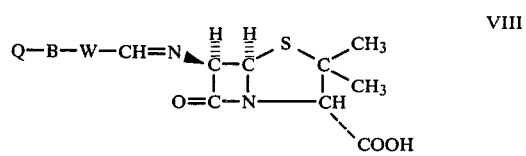

or one of its carboxylic acid salts or esters, in which B and —W— have the meaning hereinbefore defined, and Q stands for a mercapto group or a hydroxy group, as such or in the form of a salt thereof with a suitable cation, e.g. Na$^+$ or K$^+$, with a compound of formula IX:

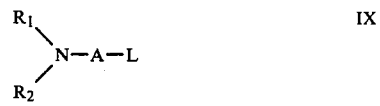

in which L stands for a halogen atom or a sulphonic acid ester group, such as mesylate or tosylate.

Similarly the compounds of formula I can be prepared by reacting a compound of formula X

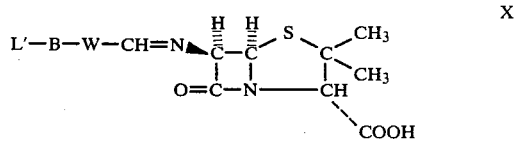

or a carboxylic acid salt or ester thereof, in which L' stands for a halogen atom or a sulphonic acid ester group, such as a tosylate, and B and —W— have the meanings defined before, with a compound of formula XI:

in which R$_1$, R$_2$, and A have the meanings defined before, and Q stands for a mercapto group or a hydroxy group, as such or in the form of one of their salts with a suitable cation, e.g. Na$^+$ or K$^+$.

The compounds of the formulae VIII and X can be produced analogous to the methods as hereinbefore described, if necessary, under temporary protection of Q by methods known from the peptide chemistry. The compounds of the formulae IX and XI are known or, if not known, can be produced similarly with the known compounds. In general, however, any known technique for establishing the —A—X—B— bonding of formula I is applicable according to the method of the invention.

Furthermore, the compounds of formula I, can be obtained from the corresponding nitro, azido or halo compounds by hydrogenation or aminolysis, respectively.

In still another embodiment of the invention the compounds of the invention in which $R_1$ and/or $R_2$ are hydrogen can be exposed to acylation or alkylation by well-known methods to form the compounds of the invention in which $R_1$ and $R_2$ have the other desired definitions given hereinbefore.

Also the radical

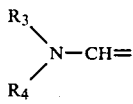

can optionally be introduced in a separate step by methods analogous to the main reaction described above for obtaining the amidinopenicillanic acid structure.

When by the above process a salt or an ester is obtained this can be transformed into the free acid in known manner and, vice versa, it will be evident that the free acid or a salt can be esterified by well-known methods.

According to one of these methods a compound of formula I can be transformed into the corresponding α-halo-alkyl ester, which then can be reacted with a salt of the acid in question to form an acyloxyalkyl ester.

It is also an object of the present invention to provide an antibacterial pharmaceutical composition for use in the treatment of infectious diseases, which contains as an active ingredient a penicillanic acid derivative of the formula I can hereinbefore.

For parenteral and topical use the compounds of formula I or their salts are preferred. These can also in some cases be used orally. However, for oral use it is in most cases advantageous to use an easily hydrolyzable ester of the compounds, because such esters are generally better absorbed than the corresponding acids or salts. The esters have no antibacterial activity per se, but they are during or after the absorption hydrolyzed with liberation of the corresponding free acids.

The active ingredient can be used as such or can be mixed up with a carrier and/or an auxiliary agent.

In such compositions, the proportion of therapeutically active material to carrier substance and auxiliary agent can vary between 1% and 95%. The compositions can either be worked up to pharmaceutical forms of presentation such as tablets, pills or dragees, or can be filled in medical containers such as capsules, or as far as suspensions are concerned filled into bottles. Pharmaceutical organic or inorganic solid or liquid carriers suitable for enteral, parenteral or topical administration can be used to make up the composition. Gelatine, lactose, starch, magnesium stearate, talc, vegetable and animal fats and oils, gum, polyalkylene glycol, or other known carriers for medicaments may all be suitable as carriers.

In the pharmaceutical compositions the compounds of the invention can be used together with other suitable therapeutically active components, preferably with other antibacterially active compounds, such as β-lactam-antibiotics, e.g. penicillins or other amidinopenicillanic acid derivatives, and cephalosporins. Also other antibacterially active substances are of interest in this connection, e.g. trimethoprim and aminoglycosides. In many cases, e.g. in combinations with penicillins like ampicillin, amoxycillin, or carbenicillin, or cephalosporins like cephalothin, cephazolin or cephalexin, a synergistic effect is observed which is of importance in many clinical situations. Also a depression of development of resistance can be obtained by a combination therapy. In such compositions the ratio between the active components appropriately is between 1:20 and 20:1, preferably within the ratio 1:5 to 5:1.

The compounds of the invention can also be used together with a β-lactamase inhibitor, such as clavulanic acid.

Another object of the invention resides in the selection of a dose of the compounds of the invention which can be administered so that the desired activity is achieved without simultaneous secondary effects.

The compounds are conveniently administered in dosage units containing amounts corresponding to from 0.01 g to 3.0 g of the free acid of formula I and preferably to from 0.05 g to 1.5 g depending on which microorganisms are involved. By the term "dosage unit" is meant a unitary, e.g. a single dose capable of being administered to a patient, and which may be readily handled and packed, remaining as a physically stable unit dose, comprising either the active material as such or a mixture of it with a pharmaceutical carrier.

Similarly, for infusion, the compounds of the invention are given in doses up to 10 g in aqueous solution.

For parenteral use, e.g. injections, the compounds of the invention are given e.g. in an aqueous solution or suspension as a dosage unit containing from 0.1 g to 1 g of the compound, calculated as the free acid to be dissolved or suspended immediately before use, or ready for use together with a pharmaceutically acceptable vehicle.

In the form of a dosage unit the compound may be administered once or more times a day at appropriate intervals, always depending, however, on the condition of the patient.

As used herein the term "patient" includes animals as well as humans.

Thus, a daily dose will preferably amount to from 0.2 g to 30 g of the compound of the invention calculated as free acid.

The compounds of the invention are appropriately administered in the form of their pharmaceutically acceptable, non-toxic, easily hydrolyzable esters.

The term "non-toxic" for easily hydrolyzable esters shall mean that such esters are therapeutically acceptable for their intended form of administration. In general the easily hydrolyzable esters of the compounds of the invention are used in the oral administration, but their use in the parenteral administration is also within the scope of the invention.

The invention will be further described in the following Examples which are not construed as limiting the invention.

EXAMPLE 1

Pivaloyloxymethyl
6-[4'-(2''-aminoethylthiomethyl)-piperidino-
methyleneamino]-penicillanate dihydrochloride

I: 4-(2'-Hydroxyethylthiomethyl)-piperidine hydrobromide (A)

To a solution of 2-mercaptoethanol (35 g, 0.45 mole) in methanol (100 ml) was added 5N potassium hydroxide in methanol (60 ml, 0.3 mole) followed by 4-bromomethylpiperidine hydrobromide (25.7 g, 0.1 mole). The mixture was stirred for 3 hours and thereafter acidified with an ethanolic solution of hydrogen bromide. Precipitated potassium bromide was removed by filtration and the filtrate taken to dryness in vacuo. Excess mercaptoethanol was removed by trituration with ether to leave a residue of crude (A) which was used without purification.

II: 4-(2'-Bromoethylthiomethyl)-piperidine hydrobromide (B)

To a cooled solution of crude (A) (30 g) in dry chloroform (200 ml), phosphorus tribromide (30 ml) was added. The mixture was stirred for 3 hours and left over night. The solvent was removed in vacuo and the residue crystallized by treament with ether. Recrystallization from ethanol gave (B) as colourless crystals with m.p. 162°–163° C.

III: 4-(2'-Azidoethylthiomethyl)-piperidine (C)

A solution of (B) (5.8 g) in methanol (20 ml) and water (20 ml) was adjusted to pH 6.5 with sodium hydrogencarbonate. Sodium azide (2.4 g) was added and the mixture refluxed for 3 hours. After cooling, methanol was removed in vacuo and the solution was made alkaline with sodium hydroxide and extracted with ether. Removal of the solvent gave (C) as a yellow oil. The IR spectrum (chloroform) showed a strong band at 2100 $cm^{-1}$.

IV: N-Formyl-4-(2'-azidoethylthiomethyl)-piperidine (D)

(C) (2.8 g) was dissolved in methyl formate (15 ml) and left at room temperature for 16 hours. The solvent was removed and the residue was purified by chromoatography on $SiO_2$ using a mixture of cyclohexane and ethyl acetate (1:1) as eluent. Pure (D) was obtained as a pale yellow oil. The IR spectrum (chloroform) showed strong bands at 1655 and 2100 $cm^{-1}$.

V: Pivaloyloxymethyl 6-[4'-(2''-azidoethylthiomethyl)-piperidino-methyleneamino]-penicillanate hydrochloride (E)

To a cooled (−30° C.), stirred solution of (D) (2.17 g) in dry chloroform (7 ml) a solution of oxalyl chloride (0.74 ml) in dry chloroform (3 ml) was dropped, maintaining a temperature of −30° C. Stirring was continued until evolution of gases ceased (20 min) whereafter the solution was dropped to a cooled (−60° C.), stirred solution of pivaloyloxymethyl 6-aminopenicillanate (2.84 g) in dry chloroform (30 ml), maintaining a temperature of −60° C. Triethylamine (2.7 ml) was added and the mixture was allowed to warm to 0° C., at which temperature it was kept for 1 hour. The solvent was removed in vacuo and the residue partitioned between water (25 ml) and ether (50 ml). The organic layer was washed with water (3×5 ml), covered with water (100 ml) and pH was adjusted to 3.0 with 1N hydrochloric acid at 0° C. The aqueous phase was separated, washed with ether and freeze-dried to give (E) as an amorphous solid. The IR-spectrum (chloroform) showed bands at 2100, 1780-45, and 1685 $cm^{-1}$.

VI: Pivaloyloxymethyl 6-[4'-(2''-aminoethylthiomethyl)-piperidino-methyleneamino]-penicillanate dihydrochloride (F)

To a stirred solution of (E) (0.5 g) in water (50 ml) and ethyl acetate (25 ml) 10% palladium on carbon (0.5 g) was added. Hydrogen was bubbled through and the pH maintained at 3.0 by simultaneous addition of 0.5N hydrochloric acid. When the consumption of acid ceased, the catalyst was filtered off, the aqueous phase was separated and freeze-dried to give (F) as an amorphous solid. The NMR-spectrum ($D_2O$, TMS as internal standard) showed peaks at $\delta=1.22$(s), 1.48(s), 1.68(s), 1.0–2.3(m), 2.5–3.0(m), 3.23(m), 3.0–4.2(m), 5.50(d, J=4), 5.65 (d, J=4), 5.78(d, J=6), 5.96(d=6), and 7.97(s).

EXAMPLE 2

6-[4'-(2''-Aminoethylthiomethyl)-piperidino-methyleneamino]-penicillanic acid hydrochloride

I: 6-[4'-(2''-azidoethylthiomethyl)-piperidino-methyleneamino]-penicillanic acid (G)

To a suspension of 6-aminopenicillanic acid (2.16 g) in dry chloroform (25 ml), trimethylchlorosilane (2.53 ml) was added. After stirring for 15 minutes, triethylamine (2.8 ml) was added. After stirring for 15 minutes, the clear solution was cooled to −60° C. and a solution of acid amide chloride, prepared from 2.5 g of (D) of Example I as described above, was added portionwise maintaining a temperatuure of −60° C. Finally, triethylamine (2.8 ml) was added and the mixture allowed to warm to 0° C. The solvent was removed in vacuo and the residue treated with dry ether (50 ml). Triethylamine hydrochloride was filtered off and the filtrate was cooled to 0° C. Water (25 ml) was added and the mixture was stirred until two clear layers resulted. The aqueous phase was separated and freeze-dried to give (G) as an amorphous solid.

II: 6-[4'-(2''-aminoethylthiomethyl)-piperidino-methyleneamino]-penicillanic acid hydrochloride (H)

To a stirred solution of (G) (0.5 g) in water (50 ml) 10% palladium on carbon (0.5 g) was added. Hydrogen was bubbled through and the ph was maintained at 5.0 by simultaneous addition of 0.5 N hydrochloric acid. When the consumption of acid ceased the catalyst was filtered off and the filtrate freeze-dried to give (H) as an amorphous solid. The IR-spectrum (KBr) showed bands at 1765, 1685, and 1600 $cm^{-1}$.

EXAMPLE 3–4

Pivaloyloxymethyl
6-[4'-(3''-aminopropylthiomethyl)-piperidino-methyleneamino]-penicillanate dihydrochloride and
6-[4'-(3''-aminopropylthiomethyl)-piperidino-methyleneamino]-penicillanic acid, hydrochloride By replacing 2-mercaptoethanol with 3-mercaptopropanol-1 in Example 1, I, and proceeding in a manner analogous to that of Examples 1 and 2, the desired compounds were obtained as amorphous solids. The IR-spectra (chloroform and KBr, respectively) showed bands at 1780–1750, 1685, and 1765, 1685, 1600 cm$^{-1}$, respectively.

EXAMPLE 5

Pivaloyloxymethyl 6-[4'-(2''-aminoethoxy)-piperidino-methyleneamino]-penicillanate dihydrochloride I: N-Benzyl-4-(carbethoxymethoxy)-piperidine (A)

To a solution of N-benzyl-4-hydroxy-piperidine (19.2 g) in dry tetrahydrofuran (100 ml), sodium hydride (2.4 g, 0.1 mole) was added and the mixture was refluxed until evolution of hydrogen ceased (1 hour). A solution of ethyl bromoacetate (18.4 g) in dry tetrahydrofuran (20 ml) was added and the mixture was refluxed for 3 hours. After standing over night, the solvent was removed in vacuo and the residue was extracted with light petroleum. The extract was concentrated to a sirup which was distilled at 0.1 mm Hg to give (A) as a colourless oil with b.p. 140°–145° C.

II: N-Benzyl-4-(2'-hydroxyethoxy)-piperidine (B)

A solution of (A) (14 g) in tetrahydrofuran (50 ml) was added to a solution of lithium aluminum hydride (2 g) in tetrahydrofuran (100 ml) under stirring. The mixture was refluxed for 3 hours and finally hydrolyzed by careful addition of water. After removal of inorganic salts by filtration, the filtrate was concentrated to give (B) as a viscous oil.

III: 4-(2'-Hydroxyethoxy)-piperidine hydrobromide (C)

A solution of (B) (12 g) in ethanol (200 ml) was neutralized with an ethanolic solution of hydrogen bromide and hydrogenated in the presence of 10% palladium on carbon (2.4 g). After 5 hours the uptake of hydrogen ceased and the catalyst was removed by filtration. The filtrate was taken to dryness in vacuo to give (C) as a semicrystalline solid.

IV: 4-(2'-Bromoethoxy)-piperidine hydrobromide (D)

(D) was prepared analogously to compound (B) in Example 1, and was obtained as a semicrystalline mass.

V: 4-(2'-Azidoethoxy)-piperidine (E)

(E) was prepared analogously to compound (C) in Example 1, and was obtained as a yellow oil.

VI: N-Formyl-4-(2'-azidoethoxy)-piperidine (F)

(F) was prepared analogously to compound (D) in Example 1, and was obtained as a pale yellow oil. The IR-spectrum (chloroform) showed strong bands at 2100 and 1650 cm$^{-1}$.

VII: Pivaloyloxymethyl 6-[4'-(2''-azidoethoxy)-piperidino-methyleneamino]-penicillanate hydrochloride (G)

(G) was prepared analogously to compound (E) in Example 1, and was obtained as an amorphous solid. The IR-spectrum (chloroform) showed bands at 2100, 1780–1745, and 1685 cm$^{-1}$.

VIII: Pivaloyloxymethyl 6-[4'-(2''-aminoethoxy)-piperidino-methyleneamino]-penicillanate dihydrochloride (H)

(H) was prepared analogously to compound (F) in Example 1, and was obtained as an amorphous solid. The NMR spectrum (D$_2$O, TMS as external standard) showed peaks at $\delta = 1.23$ (s), 1.55 (s), 1.73 (s), 1.4–2.4 (m), 3.1–4.3 (m), ca. 4.8 (s), 5.5–5.8 (m), 5.83 (d, J = 6), 6.00 (d, J = 6), and 8.07 (bs).

EXAMPLE 6

6-[4'-(2''-aminoethoxy)-piperidino-methyleneamino]-penicillanic acid hydrochloride By following the procedure of Example 2, step I and step II, but replacing the compound (D) of Example 1 with the compound (F) of Example 5, the desired compound was obtained as an amorphous solid. The IR-spectrum (KBr) showed bands at 1765, 1685, and 1600 cm$^{-1}$.

EXAMPLES 7–8

Pivaloyloxymethyl 6-[4'-(3''-aminopropoxy)-piperidino-methyleneamino]-penicillanate dihydrochloride and 6-[4'-(3''-aminopropoxy)-piperidino-methyleneamino]-penicillanic acid, hydrochloride By replacing ethyl bromoacetate with ethyl 3-bromopropionate in Example 5, step I, and proceeding in a manner analogous to Examples 5 and 2, the desired compounds were obtained as amorphous solids. The IR-spectra (chloroform and KBr, respectively) showed bands at 1780–1750, 1685, and 1765, 1685, 1600 cm$^{-1}$, respectively.

EXAMPLES 9–10

Pivaloyloxymethyl 6-[4'-(2''-aminoethoxymethyl)-piperidinomethyleneamino]-penicillanate dihydrochloride and Pivaloyloxymethyl methyleneamino 6-[4'-(3''-aminopropoxymethyl)-piperidino methyleneamino]-penicillanate dihydrochloride By replacing N-benzyl-4-hydroxy-piperidine with N-benzyl-4-hydroxymethyl-piperidine and using either ethyl bromoacetate or ethyl 3-bromopropionate and following the procedure described in Example 5, step I to VIII, the desired compounds were obtained as amorphous solids. The IR-spectra (chloroform) showed bands at 1780–1750 and 1685 cm$^{-1}$.

EXAMPLES 11–12

6-[4'-(2''-aminoethoxymethyl)-piperidino-methyleneamino]-penicillanic acid hydrochloride and 6-[4'-(3''-aminopropoxymethyl)-piperidino]methyleneamino-penicillanic acid hydrochloride By replacing N-benzyl-4-hydroxypiperidine with N-benzyl-4-hydroxymethyl-piperidine and using either ethyl bromoacetate or ethyl 3-bromopropionate and following the procedure described in Example 5, step I to VI, and thereafter the procedure described in Example 2, steps I and II, the desired compounds were obtained as amorphous solids. The IR-spectra (KBr) showed bands at 1765, 1685 and 1600 cm$^{-1}$.

EXAMPLE 13

Pivaloyloxymethyl 6-[4'-(2''-diethylaminoethylthiomethyl)-piperidino-methyleneamino]-penicillanate dihydrochloride I: 4-(2'-diethylaminoethylthiomethyl)-Piperidine (A)

To a solution of N,N-diethylaminoethylmercaptan (6.8 g, 0.05 mole) in methanol (25 ml), 5 N potassium hydroxide in methanol (16 ml) was added, followed by 4-bromomethyl-piperidine (10.3 g, 0.04 mole). The mixture was stirred for 20 hours at room temperature. Most of the methanol was removed in vacuo, and the residue was diluted with ether (100 ml). After filtration, the filtrate was washed with two 5 ml portions of 2 N sodium hydroxide and dried over sodium sulphate. The solvent was stripped in vacuo, and the residue was chromatographed on "Florisil" (120 g), eluting with ether followed by ethyl acetate-methanol (8:2) to give (A) as a faintly yellow oil.

II: Pivaloyloxymethyl 6-[4'-(2''-diethylaminoethylthiomethyl)-piperidinomethyleneamino]-penicillanate dihydrochloride (B)

A mixture of freshly prepared isopropyl formimidate hydrochloride (1.24 g, 0.01 mole) and pivaloyloxymethyl 6-aminopenicillanate (3.3 g, 0.01 mole) in dry chloroform (50 ml) was stirred for 10 minutes at room temperature. After cooling to 5° C., (A) (2.3 g, 0.01 mole) was added in one portion, and the mixture was left at 5° C. for 20 hours. After washing with dilute sodium hydrogen carbonate followed by water, fresh water (50 ml) was added, and the pH adjusted to 3.0 with hydrochloric acid. The aqueous phase was separated, filtered and freeze-dried to give (B) as a nearly colourless, amorphous powder. The NMR spectrum (D$_2$O, TMS as external standard) showed peaks at $\delta = 1.22$ (s), 1.32 (t, J=7), 1.53 (s), 1.72 (s), 1.4–2.4 (m), 2.6–4.3 (m), 3.28 (q, J=7), 4.70 (s), 5.50 (d, J=4), 5.67 (d, J=4), 5.80 (d, J=6), 5.95 (d, J=6), and 7.97 (s).

EXAMPLE 14

Pivaloyloxymethyl 6-[4'-(1''-(2'''-diethylaminoethylthio)-ethyl)piperidinomethyleneamino]-penicillanate dihydrochloride I: 4-(1'-bromoethyl)-piperidine hydrobromide (A)

A solution of 4-(1'-hydroxyethyl)-piperidine (13 g, m.p. 65°–68° C.) in ethanol (25 ml) was neutralized with 5 N hydrogen bromide in ethanol. After removal of the solvent in vacuo, the residue was distilled twice with chloroform and finally dried at 0.05 mm Hg. The oily residue was mixed with phosphorous tribromide (25 ml) and heated on the steam bath for 2 hours. After cooling, the mixture was treated with ether (250 ml) to give a crystalline precipitate which was filtered off and washed with ether to give (A) as hygroscopic crystals. Recrystallization from acetonitrile gave material with m.p. 146°–48° C.

II: N-Formyl-4-(1'-bromoethyl)-piperidine (B)

(A) (25 g) was dissolved in water (10 ml). Methyl formate (50 ml) and potassium carbonate (25 g) were added, and the mixture stirred for 20 hours. The solvent was decanted, and the residue was extracted with two 50 ml portions of ether. The combined organic phases were washed with water, dried and evaporated to give (B) as a colourless oil. The IR spectrum (chloroform) showed a strong band at 1650 cm$^{-1}$.

III: N-Formyl-4-(1'-(2''-diethylaminoethylthio)ethyl)piperidine (C)

To a solution of N,N-diethylaminoethylmercaptan (4 g, 0.03 mole) in methanol (10 ml), 5 N potassium hydroxide in methanol (5 ml) was added, followed by (B) (5.5 g, 0.025 mole). The mixture was heated to 40° C. for 20 hours. After removal of the solvent in vacuo, the residue was diluted with ether (50 ml) and filtered. The filtrate was washed with two 5 ml portions of 2 N sodium hydroxide followed by water and dried. The solvent was stripped in vacuo, and the residue was chromatographed on "Florisil" (100 g), eluting with ether followed by ethyl acetate-methanol (8:2) to give (C) as a faintly yellow oil.

IV: Pivaloyloxymethyl 6-[4'-(1''-(2'''-diethylaminoethylthio)-ethyl)piperidinomethyleneamino]-penicillanate dihydrochloride (D)

(D) was prepared analogously to compound (E) in Example 1. The preparation of the chloroformiminocompound was performed at −50° C. in order to suppress side-reactions leading to coloured products. The primarily obtained dihydrochloride was strongly yellow and was purified by chromatography on Diaion ® HP20 in aqueous solution. (D) was obtained as a faintly yellow, amorphous powder. The NMR spectrum (D$_2$O, TMS as external standard) showed peaks at $\delta = 1.20$ (s), 1.53 (s), 1.73 (s), 1.30 (d), 1.32 (t, J=7), 1.4–2.3 (m), 3.30 (q, J=7), 2.8–4.4 (m), ca. 4.6 (s), 5.53 (d, J=4), 5.70 (d, J=4), 5.83 (d, J=6), 5.98 (d, J=6), and 8.0 (s).

EXAMPLE 15

Pivaloyloxymethyl 6-[4'-(2''-aminoethoxy)-hexahydro-1H-azepin-1-ylmethyleneamino]-penicillanate dihydrochloride I: N-Benzyl-hexahydro-4H-azepin-4-ethyleneketal (A)

To a stirred suspension of N-benzyl-hexahydro-4H-azepin-4-on hydrochloride (36 g, 0.15 mole) in ethylene glycol (60 ml), boron trifluoride diethyl etherate (25 ml) was added. After stirring for 30 minutes, a clear solution was formed. After standing for 2 hours, the solution was diluted with ether (150 ml) and washed successively with 2 N sodium hydroxide (250 ml) and water. After drying, the ether was removed to give the title compounds as a colourless oil. The IR spectrum (chloroform) showed no absorption in the carbonyl region.

II: N-Benzyl-4-(2'-hydroxyethoxy)-1H-azepin (B)

To a cold solution of anhydrous aluminium chloride (16 g) in dry ether (120 ml), a solution of lithium aluminium hydride (1.6 g) in dry ether (120 ml) was added. After stirring for 15 minutes, a solution of (A) (25 g) in dry ether (100 ml) was added portionwise, and the mixture was refluxed for 1 hour. After cooling, water (4 ml) was added carefully, followed by 12 N potassium hydroxide (35 ml). The ether layer was decanted and the precipitate was extracted with eight 100 ml portions of ether. The combined ether extracts were dried over sodium sulphate, and the solvent was removed in vacuo. The residue was chromatographed on "Florisil" (200 g), eluting first with methylenechloride followed by ether to give impure (B), which was further purified by gelfiltration on Sephadex ® LH 20, using chloroform-hexane (65:35) as solvent. Pure (B) was obtained as a faintly coloured oil. The NMR spectrum (CDCl$_3$, TMS as internal standard) showed peaks at $\delta = 1.5$–2.2 (m), 2.3–3.0 (m), 3.3–4.0 (m), 3.62 (s), and 7.32 (s).

III: 4-(2'-hydroxyethoxy)-1H-azepin hydrobromide (C)

To a suspension of (B) (7.5 g) in water (20 ml), 1 N hydrobromic acid (30 ml) was added. The clear solution was hydrogenated over 10% palladium on carbon catalyst (4 g). After 3 hours the consumption of hydrogen ceased; the catalyst was filtered off, and the filtrate taken to dryness in vacuo. The residue was distilled twice with chloroform to give (C) as a viscous oil.

IV: 4-(2'-bromoethoxy)-1H-azepin hydrobromide (D)

To a suspension of (C) (8 g) in dry chloroform, phosphorous tribromide (8 ml) was added. The mixture was stirred for 24 hours at room temperature. The solvent was stripped in vacuo, and the residue was triturated with five 50 ml portions of dry ether, and finally dried in vacuo to give (D) as a viscous oil.

V: N-Formyl-4-(2'-bromoethoxy)-1H-azepin (E)

To a solution of (D) (10 g) in water (5 ml), methyl formate (50 ml) and potassium carbonate (10 g) were added. The mixture was stirred for 24 hours, and the organic phase was decanted. The residue was extracted twice with methyl formate. The combined organic solutions were concentrated in vacuo, and the residue was dissolved in ether, dried and chromatographed on silica gel (50 g) with ether as eluent to give (E) as a colourless oil. The IR spectrum (chloroform) showed a strong band at 1650 cm$^{-1}$.

VI: N-Formyl-4-(2'-azidoethoxy)-1H-azepin (F)

To a solution of (E) (2.7 g) in methanol (15 ml), lithium azide (1.65 g) was added. The solution was refluxed for 6 hours and left over night at room temperature. The solvent was removed in vacuo, and the residue was extracted with three 15 ml portions of chloroform to give crude (F) which was purified by chromatography on silica gel with ethyl acetate as eluent. Pure (F) was obtained as a colourless oil. The IR spectrum (chloroform) showed strong bands at 2100 and 1650 cm$^{-1}$.

VII: Pivaloyloxymethyl 6-[4'-(2''-azidoethoxy)-hexahydro-1H-azepin-1-yl-methyleneamino]-penicillanate hydrochloride (G)

(G) was prepared analogously to compound (E) in Example 1 and was obtained as an amorphous solid. The IR spectrum (chloroform) showed bands at 2100, 1780-1750, and 1675 cm$^{-1}$.

VIII: Pivaloyloxymethyl 6-[4'-(2''-aminoethoxy)-hexahydro-1H-azepin-1-yl-methyleneamino]-penicillanate dihydrochloride (H)

(H) was prepared analogously to compound (F) in Example 1 and was obtained as an amorphous solid. The NMR spectrum (D$_2$O, TMS as external standard) showed peaks at δ=1.23 (s), 1.53 (s), 1.73 (s), 1.5-2.4 (m), 3.1-4.1 (m), 4.75 (s), 5.55 (d, J=4), 5.70 (d, J=4), 5.82 (d, J=6), 5.97 (d, J=6), and 8.10 (m).

EXAMPLE 16

Pivaloyloxymethyl 6-[4'-(2'''-acetamidoethoxy)-piperidino-methyleneamino]-penicillanate hydrochloride A stirred solution of pivaloyloxymethyl 6-[4'-(2''-aminoethoxy)-piperidino-methyleneamino]-penicillanate dihydrochloride (557 mg, 0.001 mole) in dry chloroform (10 ml) was cooled to −50° C. Acetyl chloride (1 ml of a 1 M solution in dry chloroform) was added, followed by triethylamine (3 ml of a 1 M solution in dry chloroform). After stirring for 5 minutes, the solvent was removed in vacuo, and the residue distributed between ethyl acetate (10 ml) and water (10 ml). The organic layer was washed with water (5 ml), dried and stripped in vacuo. The residue was dissolved in ether (10 ml), water (10 ml) was added and pH adjusted to 3.0 with 0.25 N hydrochloric acid. The aqueous phase was separated and freeze-dried to give the title compound as a white, amorphous powder. The IR spectrum (KBr) showed bands at 1780-1750, 1685, 1650, and 1540 cm$^{-1}$.

EXAMPLE 17

Pivaloyloxymethyl 6-[4'-(2''-benzamidoethoxy)piperidino-methyleneamino]-penicillanate hydrochloride By replacing acetyl chloride with benzoyl chloride and following the procedure in the above example, the title compound was obtained as a white, amorphous solid. The IR-spectrum (KBR) showed bands at 1780-1750, 1685, 1640, and 1530 cm$^{-1}$.

EXAMPLE 18

Pivaloyloxymethyl 6-[4'-(2''-diethylaminoethylthiomethyl)piperidino-methyleneamino]-penicillanate dihydrochloride I: N-Formyl-4-bromomethylpiperidine (A)

To a solution of 4-bromomethylpiperidin hydrobromide (12.8 g, 0.05 mole) in water (5 ml), methyl formate (25 ml) and potassium carbonate (10 g) were added and the mixture stirred for 20 hours. The solvent was decanted, and the residue was extracted with two 25 ml portions of ether. The combined organic phases were washed with water, dried and evaporated to give (A) as a colourless oil. The IR spectrum (chloroform) showed a strong band at 1650 cm$^{-1}$.

II: Pivaloyloxymethyl 6-[4'-bromomethylpiperidino-methyleneamino]-penicillanate hydrochloride (B)

(B) was prepared analogously to compound (F) in Example 1, and was obtained as an amorphous solid. The IR spectrum (chloroform) showed bands at 1780-1750, and 1685 cm$^{-1}$.

III: Pivaloyloxymethyl 6-(4'-(2''-diethylaminoethylthiomethyl)-piperidino-methyleneamino)-penicillanate dihydrochloride (C)

To a solution of N,N-diethylaminoethylmercaptan (0.266 g, 0.002 mole) in methanol (5 ml), N methanolic potassium hydroxyde (2 ml) was added. The solution was concentrated in vacuo to a sirup and ethyl acetate was added, followed by (B) (0.555 g, 0.001 mole). After stirring for 3 hours at room temperature, the mixture was diluted with ether (20 ml), and the organic layer was washed with five 2 ml portions of water. Water (10 ml) was added to the organic phase, and pH was adjusted to 3.0 with dilute hydrochloric acid. The aqueous phase was separated and freeze-dried to give crude (C), which was purified by chromatography on Diaion ® HP 20 in aqueous solution. (C) was obtained as an almost white, amorphous solid, identical in every respect with compound (B) of Example 13.

EXAMPLE 19

Pivaloyloxymethyl 6-[(7-(2-aminoethylthiomethyl)-3azabicyclo[3.3.1]nonyl-3)-methyleneamino]-penicillanate dihydrochloride By substituting 7-bromomethyl-3-azabicyclo[3.3.1]nonane hydrobromide for the 4-bromomethyl-piperidine hydrobromide used in Example 1, step I, and following the procedure of the steps I to VI, the title compound was obtained as an amorphous powder. The IR-spectrum showed strong bands at 1780–1750 and 1685 cm$^{-1}$.

EXAMPLE 20

Pivaloyloxymethyl 6-[(9-(2-aminoethylthiomethyl)-3-azaspiro[5.5]undecyl-3')-methyleneamino]-penicillanate, dihydrochloride By substituting 9-bromomethyl-3-azaspiro[5.5]undecane, hydrobromide for the 4-bromomethylpiperidine, hydrobromide used in Example 1, step I, and following the procedure of the steps I to VI, the title compound was obtained as an amorphous powder. The IR-spectrum showed strong bands at 1780–1750 and 1680 cm$^{-1}$.

EXAMPLE 21

Pivaloyloxymethyl 6-[4'-(2''-aminoethylthiomethyl)-piperidino-methyleneamino]-penicillanate dihydrochloride I: 2-(tert-butoxycarbonylamino)-ethylmercaptan (A)

To a solution of 2-aminoethylmercaptan hydrochloride (11.4 g, 0.1 mole) in methanol (100 ml), triethylamine (14 ml) was added, followed by di-tert-butyl dicarbonate (24 g). After standing for 1 hour at room temperature, the solvent was stripped in vacuo, and the residue was treated with ethyl acetate. Triethylamine hydrochloride was filtered off, and the filtrate was evaporated to dryness, leaving (A) as a colourless oil.

II: N-Formyl-4-(2'-(tert-butoxycarbonylamino)-ethylthiomethyl)-piperidine (B)

To a solution of (A) (5.3 g, 0.03 mole) in methanol (10 ml), 5 N potassium hydroxide in methanol (5 ml) was added, followed by N-formyl-4-bromomethylpiperidine (5.2 g, 0.025 mole). The mixture was left at room temperature for 20 hours. After removal of the solvent in vacuo, the residue was diluted with ether (50 ml) and filtered. The filtrate was washed with two 5 ml portions of 2 N sodium hydroxide, followed by water and dried. The solvent was stripped in vacuo, and the residue was chromatographed on silica gel (100 g), eluting with ether to give (B) as a colourless oil.

III: Pivaloyloxymethyl 6-[4'-(2''-(tert-butoxycarbonylamino)-ethylthiomethyl)-piperidino-methyleneamino]-penicillanate hydrochloride (C)

(C) was prepared analogously to compound (E) in Example 1 and was obtained as a freeze-dried, amorphous solid.

IV: Pivaloyloxymethyl 6-[4'-(2''-aminoethylthiomethyl)-piperidino-methyleneamino]-penicillanate dihydrochloride (D)

(C) (500 mg) was dissolved in trifluoroacetic acid (2 ml). After 1 minute, the solution was poured into a stirred mixture of sodium hydrogen carbonate solution (50 ml) and ethyl acetate (25 ml). The organic layer was separated, water (25 ml) was added, and pH adjusted to 3.0 with dilute hydrochloric acid. The aqueous layer was separated and freeze-dried to give (D) as a colourless, amorphous solid, identical in every respect with compound (F) of Example 1.

What we claim is:

1. A 6β-amidinopenicillanic acid of the general formula I:

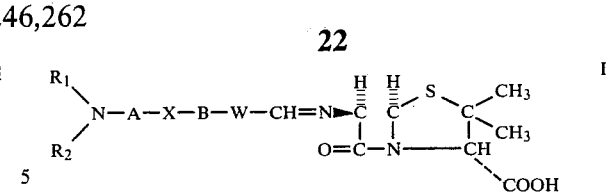

in which X stands for an oxygen or a sulphur atom, —A— stands for a straight or branched, aliphatic hydrocarbon chain, containing from 2 to 4 carbon atoms, or —A— can be a single bond, and —B— stands for a straight or branched, saturated or unsaturated aliphatic hydrocarbon radical, containing from 1 to 4 carbon atoms, or —B— can be a single bond; $R_1$ and $R_2$ stand for hydrogen, or a lower alkyl radical containing from 1 to 4 carbon atoms, a phenyl or phenyl-lower alkyl radical; and $R_2$ further stands for an acyl radical derived from a mono- or dibasic carboxylic acid, sulphuric acid, a sulphonic acid, a sulphinic acid, phosphoric acid, or a phosphoric acid, or $R_2$ can represent an unsubstituted or a lower alkyl or phenyl substituted radical selected from the group consisting of carbamoyl, guanyl and guanylcarbamoyl radicals; or $R_1$ and $R_2$ together with the nitrogen atom can form a monocyclic saturated ring having from 4 to 8 carbon atoms; and furthermore $R_1$ and $R_2$ together can represent a radical of the formula

in which $R_3$ and $R_4$ each stands for hydrogen, lower alkyl, phenyl, or phenyl-lower alkyl radicals, or in which $R_3$ and $R_4$ together with the nitrogen atom form a monocyclic, saturated ring having from 4 to 8 carbon atoms; and in which the radical —W— stands for the groupings:

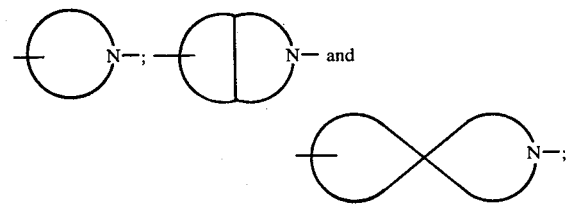

which represent saturated, monocyclic, bicyclic or spirocyclic ring systems, respectively, containing from 4 to 11 carbon atoms in total; and salts of the compounds of the formula I with pharmaceutically acceptable, non-toxic organic and inorganic and inorganic acids or bases, and easily hydrolyzable, pharmaceutically acceptable, non-toxic esters of the penicillanic acid derivatives of formula I and salts of such esters with pharmaceutically acceptable, non-toxic acids or bases.

2. A compound according to claim 1, in which —W— stands for

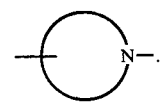

3. A compound according to claim 1, in which —W— stands for

4. A compound according to claim 1, in which —W— stands for

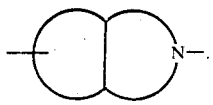

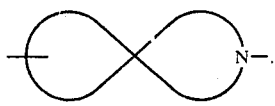

5. A compound according to claim 1, in which X stands for oxygen.

6. A compound according to claim 1, in which X stands for sulphur.

7. A compound according to claim 1, in which —A— stands for a single bond.

8. A compound according to claim 1, in which —B— stands for a single bond.

9. A compound according to claim 1, in which —B— stands for a straight or branched, saturated or unsaturated hydrocarbon radical containing from 1 to 4 carbon atoms.

10. A compound according to claim 2, in which $R_1$ and $R_2$ are selected from the group consisting of hydrogen and lower alkyl containing from 1 to 4 carbon atoms;

A is a single bond or is a straight or branched carbon chain containing 2-4 carbon atoms, the

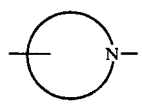

represents a saturated monocyclic ring containing 4-8 carbon atoms, and pharmaceutically acceptable, non-toxic salts and easily hydrolyzable, non-toxic, pharmaceutically acceptable esters thereof and their salts.

11. A compound according to claim 10, in which —A— is an ethylene, propylene, butylene, isopropylene, isobutylene or sec-butylene radical; or —A— is a single bond.

12. A compound according to claim 9, in which —B— is a methylene, ethylene, propylene, trimethylene, tetramethylene, propylidene, methyltrimethylene, vinylene, propenylene, butenylene, methylpropenylene, propynylene, butynylene, methylpropynylene radical, ethanylylidene or propanylylidene, or —B— is a single bond.

13. A compound as in claim 10 wherein $R_1$ and $R_2$ are hydrogen or methyl.

14. A compound as in claim 10 wherein $R_1$ and $R_2$ are both hydrogen.

15. A compound as in claim 10 wherein A is a straight carbon atom chain containing 2-3 carbon atoms.

16. A compound as in claim 10 wherein A is a branched carbon chain containing 2-4 carbon atoms.

17. A compound as in claim 10 wherein the group

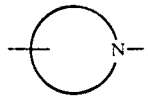

contains 5 or 6 carbon atoms.

18. A compound as in claim 17 wherein the group

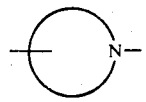

is piperidyl-1.

19. A compound as in claim 17 wherein the group

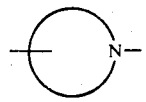

is hexahydro-1H-azepin-1-yl.

20. A compound according to claim 2 in which —A— stands for a carbon chain containing from 2 to 3 carbon atoms, $R_1$ and $R_2$ stand for hydrogen, and pharmaceutically acceptable, non-toxic salts and easily hydrolyzable esters thereof, and their salts.

21. 6-[4'-(2''-aminoethylthiomethyl)-piperidinomethyleneamino]-penicillanic acid and pharmaceutically acceptable, non-toxic salts and easily hydrolyzable esters thereof and salts of said esters.

22. 6-[4'-(2''-aminoethoxy)-piperidinomethyleneamino]-penicillanic acid and pharmaceutically acceptable, non-toxic salts and easily hydrolyzable esters thereof and salts of said esters.

23. 6-[4'-(2''-diethylaminoethylthiomethyl)-piperidino-methyleneamino]-penicillanic acid and pharmaceutically acceptable, non-toxic salts and easily hydrolyzable esters thereof and salts of said esters.

24. 6[4'-(1''-(2'''-diethylaminoethylthio)-ethyl)-piperidino-methyleneamino]-penicillanic acid and pharmaceutically acceptable, non-toxic salts and easily hydrolyzable esters thereof and salts of said esters.

25. 6-[4'-(2''-aminoethoxy)-hexahydro-1H-azepin-1-yl-methyleneamino]-penicillanic acid and pharmaceutically acceptable, non-toxic salts and easily hydrolyzable esters thereof and salts of said esters.

26. A compound according to claim 3 in which —A— stands for a single bond or for a carbon chain containing from 2 to 4 carbon atoms, and in which $R_1$ and $R_2$ stand for hydrogen, and pharmaceutically acceptable, non-toxic salts and easily hydrolyzable esters thereof, and their salts.

27. A compound according to claim 3 in which in the grouping

-continued

the individual rings have a maximum of 7 carbon atoms, —A— contains from 2 to 4 carbon atoms, and pharmaceutically acceptable, non-toxic salts and easily hydrolyzable esters thereof, and their salts.

28. A compound according to claim 27 in which the numbers of carbon atoms in the heterocyclic part of the ring is 4, and the total number of the carbon atoms in the ring system are 7 or 8.

29. A compound according to claim 4 in which —A— stands for a single bond or for a carbon chain containing from 2 to 4 carbon atoms, and in which $R_1$ and $R_2$ stand for hydrogen, and pharmaceutically acceptable, non-toxic salts and easily hydrolyzable esters thereof, and their salts.

30. A compound according to claim 4 in which, in the spirocyclic grouping

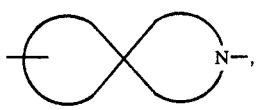

the individual rings have a maximum of 7 carbon atoms, —A— contains from 2 to 4 carbon atoms, and pharmaceutically acceptable, non-toxic salts and easily hydrolyzable esters thereof, and their salts.

31. A salt of a compound of formula I of claim 1, which is a zwitterion or a mono- or dibasic salt, formed with hydrochloric acid, phosphoric acid, nitric acid, p-toluenesulphonic acid, acetic acid, propionic acid, citric acid, tartaric acid, or maleic acid or another antibiotic with acidic character.

32. A salt of a compound of formula I of claim 1, which is a salt with an alkali metal an alkaline earth metal, with ammonia or triethylamine, hydroxylower alkylamines, cycloalkylamines, or another antibiotic with basic character.

33. A salt as claimed in claim 32 wherein the hydroxy-lower alkylamines are selected from the group consisting of 2-hydroxyethylamine, bis-(2-hydroxyethyl)-amine or tris-(2-hydroxyethyl)-amine, the cycloalkylamine is dicyclohexylamine and the benzylamines are selected from the group consisting, of N,N'-dibenzyl-ethylenediamine, and dibenzylamine.

34. An easily hydrolyzable, pharmaceutically acceptable, non-toxic ester of a compound of formula I of claim 1, which ester is selected from the group consisting of alkanoyloxyalkyl esters, alkoxycarbonyloxyalkyl esters, lactonyl esters, lower alkoxymethyl and acylaminomethyl esters; the benzyl ester, the cyanomethyl ester, and 1-carbalkoxy-2-oxopropyl esters.

35. An antibacterial composition in dosage unit form for enteral or parenteral treatment of patients which comprises as an active ingredient 0.01 g to 3 g of a compound as claimed in claim 1 calculated as the free acid together with an non-toxic pharmaceutically acceptable carrier.

36. An antibacterial composition in dosage unit form as claimed in claim 35 for oral treatment of patients, and containing from 0.05 g to 1.5 g of the active ingredient, calculated as the free acid.

37. An antibacterial composition in dosage unit form as claimed in claim 36 and containing as the active component the compound 6-[4'-(2''-aminoethylthiomethyl)-piperidino-methyleneamino]-penicillanic acid, or a pharmaceutically acceptable, non-toxic salt or easily hydrolyzable ester thereof, or a salt of said ester.

38. An antibacterial composition in dosage unit form as claimed in claim 37 in the form of tablets, pills or capsules.

39. An antibacterial composition in dosage unit form for parenteral treatment of patients, and containing from 0.1 g to 1 g of a compound as claimed in claim 1, calculated as the free acid, as such or in the form of one of its now toxic salts.

40. An antibacterial composition containing as the active component a compound as claimed in claim 1 together with carrier substances and auxilliary agents, containing from 1% to 95% of the active component, calculated as the free acid.

41. An antibacterial composition as claimed in claim 40 containing the active component together with an active additive selected from the group consisting of known penicillins, cephalosporins, amidinopenicillanic acid derivatives, aminoglycoside antibiotics, trimethoprim or clavulanic acid, the ratio between the active compounds being between 1:20 and 20:1.

42. An antibacterial composition as claimed in claim 41 in dosage unit form for enteral and parenteral treatment of patients and containing from 0.01 g to 3 g in total of the active components, as present, in the composition.

43. The pharmaceutical composition as claimed in claim 41 wherein the ratio between the active compounds is between 1:5 and 5:1.

44. A compound according to claim 1 wherein the easily hydrolyzable, pharmaceutically acceptable, non-toxic esters of the penicillanic acid derivatives of formula I are diesters of the formula II:

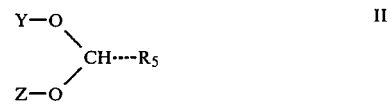

in which Y and Z can be the same or different and stand for an acyl radical of a compound of formula I, and Z furthermore can be the acyl radical of other known β-lactam derivatives, $R_5$ stands for hydrogen, methyl, ethyl, or phenyl, and salts of such esters with pharmaceutically acceptable, non-toxic acids or bases.

45. An ester as claimed in claim 44 wherein the β-lactam derivative is selected from the group consisting of penicillins, cephalosporins, amidinopenicillanic acids, amidino-$\Delta^3$-cephemcarboxylic acids and calvulanic acid.

46. A method of treating patients suffering from bacterial infections, which comprises administering to said patients a compound as claimed in claim 1, alone or in combination with another active ingredient in daily doses from 0.2 to 30 g of said compounds and said active ingredient, the weight of said compound being calculated as the free acid.

* * * * *

UNITED STATES PATENT AND TRADEMARK OFFICE
CERTIFICATE OF CORRECTION

PATENT NO. : 4,246,262  Page 1 of 4
DATED : January 20, 1981
INVENTOR(S) : Ib Steen Vangedal It is certified that error appears in the above-identified patent and that said Letters Patent are hereby corrected as shown below:

Title page, "Assignee" designation "Leo Pharmaceutical Products Ltd. A/S, Ballerup, Denmark" should read --Leo Pharmaceutical Products Ltd. A/S (Lovens kemiske Fabrik Produktion-Saktieselskab) Ballerup, Denmark--.

IN THE ABSTRACT:

The structure of formula I

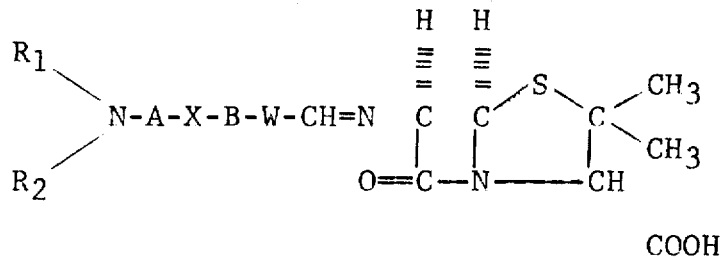

should appear as follows:

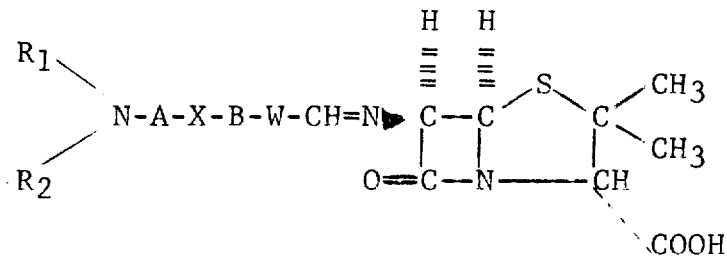

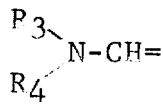　　　　should read:　　　　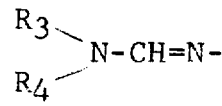

UNITED STATES PATENT AND TRADEMARK OFFICE
CERTIFICATE OF CORRECTION

PATENT NO. : 4,246,262        Page 2 of 4
DATED      : January 20, 1981
INVENTOR(S): Ib Steen Vangedal It is certified that error appears in the above-identified patent and that said Letters Patent are hereby corrected as shown below:

IN THE ABSTRACT (cont'd)

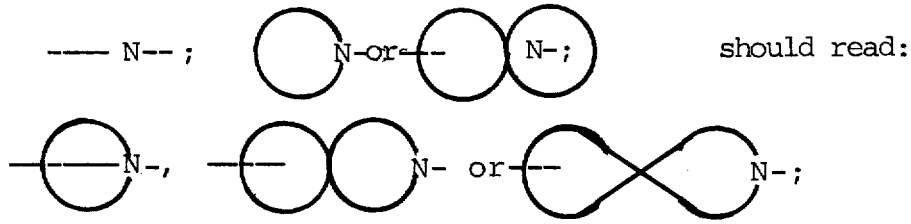   should read:

IN THE SPECIFICATION:

Col. 1, line 18, in the formula, "≡C C≡" should read --≡C-C≡/--

Col. 2, line 23 and continuing to line 24, "phenylg-lycyl" should read --phenyl-glycyl--.

Col. 3, line 4 and continuing to line 5, "2-azas-piro" should read --2-aza-spiro--.

line 40 and continuing to line 41, "pivaloy-loxymethyl" should read --pivalo-yloxymethyl--.

line 44, "ethoxycarbonyloxyethyl" should read --1-ethoxycarbonyloxyethyl--.

Col. 5, line 4, delete "methylene" and insert it under 2-methyltri-, in the last line of Col. 4 in the table under the heading -A-.

Col. 6, Line 13, "o.4" should read --0.4--.

UNITED STATES PATENT AND TRADEMARK OFFICE
CERTIFICATE OF CORRECTION

PATENT NO. : 4,246,262

DATED : January 20, 1981

INVENTOR(S) : Ib Steen Vangedal

It is certified that error appears in the above-identified patent and that said Letters Patent are hereby corrected as shown below:

Col. 6, line 15, "0.05" (1st occurrence) should be under column heading "Mecillinam" and "0.05 (2nd occurrence) should be under column heding "Compound of Example 2."

Col. 9, lines 62 and 63, "p-halo-, p-nitro-, or p-methylbenzyloxycarbonyl" should read --p-halo-, p-nitro-, and p-methoxybenzyloxycarbonyl--.

line 67, "o-nitrophenylsulphenyl" should read --o-nitrophenylsulphenyl--.

Col. 11, line 41, "can" should read --given--.

Col. 13, line 26, "treament" should read --treatment--.

Col. 14, line 19, "(d=6)," should read --(d, J=6,)-- line 36, "temperatuure" should read --temperature-- line 52, "ph" should read --pH--

Col. 16, line 33, after "Pivaloyloxymethyl" delete --methyleneamino--

Col. 20, line 62, "-3azabicyclo..." should read --3-azabicyclo...--.

UNITED STATES PATENT AND TRADEMARK OFFICE
CERTIFICATE OF CORRECTION

PATENT NO. : 4,246,262  Page 4 of 4
DATED : January 20, 1981
INVENTOR(S) : Ib Steen Vangedal It is certified that error appears in the above-identified patent and that said Letters Patent are hereby corrected as shown below:

IN THE CLAIMS:

Col. 22, line 2, "▶C̿ C̿/" should read --▶C̿-C̿/--

Col. 22, line 20, "phosphoric" should read --phosphonic-- line 54, after the word "organic" delete the words --and inorganic--

Col. 24, line 66, "thegrouping" should read --the grouping--

Col. 26, line 16, "now" should read --non-- line 56, "caphalosporins" should read --cephalosporins-- line 57, "and" should read --or--; "calvulanic" should read --clavulanic--

Signed and Sealed this

First Day of December 1981

[SEAL]

Attest:

GERALD J. MOSSINGHOFF

*Attesting Officer*   *Commissioner of Patents and Trademarks*